US011268046B2

(12) United States Patent
Mehra et al.

(10) Patent No.: US 11,268,046 B2
(45) Date of Patent: Mar. 8, 2022

(54) WATER-SOLUBLE REFILL DOSE ARTICLE ENCLOSING A CONCENTRATED LIQUID CLEANSER COMPOSITION AND KITS HAVING SAME

(71) Applicants: Curan Mehra, New York, NY (US); HAYDEN PRODUCTS LLC, New York, NY (US)

(72) Inventors: Curan Mehra, New York, NY (US); Konstantinos Lahanas, Paramus, NJ (US)

(73) Assignee: HAYDEN PRODUCTS LLC, New York, NY (US)

(*) Notice: Subject to any disclaimer, the term of this patent is extended or adjusted under 35 U.S.C. 154(b) by 0 days.

(21) Appl. No.: 17/173,433

(22) Filed: Feb. 11, 2021

(65) Prior Publication Data

US 2021/0246396 A1 Aug. 12, 2021

Related U.S. Application Data

(60) Provisional application No. 62/975,510, filed on Feb. 12, 2020.

(51) Int. Cl.

| | |
|---|---|
| ***C11D 17/04*** | (2006.01) |
| ***C11D 1/10*** | (2006.01) |
| ***C11D 1/29*** | (2006.01) |
| ***A61Q 5/02*** | (2006.01) |
| ***A61Q 19/10*** | (2006.01) |

(Continued)

(52) U.S. Cl.
CPC .................. *C11D 1/29* (2013.01); *C11D 1/37* (2013.01); *C11D 17/04* (2013.01); *C11D 17/041* (2013.01)

(58) Field of Classification Search
None
See application file for complete search history.

(56) References Cited

U.S. PATENT DOCUMENTS

| | | | |
|---|---|---|---|
| 5,224,601 | A | 7/1993 | Gouge et al. |
| 6,840,408 | B1 | 1/2005 | Foster et al. |
| 6,923,346 | B2 | 8/2005 | Foster et al. |

(Continued)

FOREIGN PATENT DOCUMENTS

| | | |
|---|---|---|
| EP | 556957 | 8/1993 |

OTHER PUBLICATIONS https://brandless.com/ products/refillable-tub-tile-cleaner-summer-breeze.

(Continued)

*Primary Examiner* — Lorna M Douyon
(74) *Attorney, Agent, or Firm* — Martin & Ferraro, LLP

(57) ABSTRACT

Water-soluble refill dose articles have a water-soluble film defining a first compartment enclosing a concentrated cleanser composition. The concentrated liquid cleanser composition comprises an anionic surfactant, 0.1% by weight to 10% by weight water, and 20% or less by weight glycol. The anionic surfactant contributes to the % by weight water, and adding the article to water at a 1:1 to 1:20 ratio defines a cleanser volume and produces a liquid cleanser that is dispensable through a pump that forms foamed cleanser and has a viscosity within a range of 1 cps to 1000 cps. Kits having a dispenser and the water soluble refill dose article are disclosed that have a pump that can foam the liquid cleanser.

18 Claims, 1 Drawing Sheet

(51) Int. Cl.
*A61K 9/12* (2006.01)
*C11D 1/37* (2006.01)

(56) References Cited

U.S. PATENT DOCUMENTS

| | | | | |
|---|---|---|---|---|
| 7,013,623 | B2 | 3/2006 | Fisher et al. | |
| 7,625,856 | B2 | 12/2009 | Burt et al. | |
| 8,105,994 | B2 | 1/2012 | Tsaur et al. | |
| 8,113,729 | B2 | 2/2012 | Solan | |
| 8,236,747 | B2 | 8/2012 | Holzhauer et al. | |
| D702,130 | S | 4/2014 | Handy | |
| 8,992,632 | B2 | 3/2015 | Holzhauer | |
| 9,237,831 | B1 * | 1/2016 | Luu | C11D 17/046 |
| 10,047,327 | B2 | 8/2018 | Keuleers et al. | |
| 10,066,195 | B2 | 9/2018 | Keuleers et al. | |
| 10,144,908 | B2 | 12/2018 | Chandar et al. | |
| 2001/0049345 | A1 | 12/2001 | Mumoli | |
| 2003/0077005 | A1 | 4/2003 | Fisher et al. | |
| 2003/0161796 | A1 | 8/2003 | Bracken et al. | |
| 2004/0115137 | A1 | 6/2004 | Verrall et al. | |
| 2004/0229763 | A1 | 11/2004 | Hutton et al. | |
| 2005/0205574 | A1 | 9/2005 | Lambotte | |
| 2007/0158367 | A1 | 7/2007 | Lin | |
| 2008/0051314 | A1 | 2/2008 | Wenzel et al. | |
| 2009/0176683 | A1 * | 7/2009 | Choe | C11D 17/0043 510/378 |
| 2010/0093581 | A1 | 4/2010 | Winston et al. | |
| 2011/0123608 | A1 | 5/2011 | McAllister et al. | |
| 2011/0278194 | A1 * | 11/2011 | Zhu | C11D 3/2079 206/524.7 |
| 2011/0288000 | A1 * | 11/2011 | Crawford | C11D 17/0026 510/403 |
| 2012/0034314 | A1 | 2/2012 | Levison et al. | |
| 2013/0277211 | A1 * | 10/2013 | Joshi | C25B 9/00 204/275.1 |
| 2014/0124535 | A1 * | 5/2014 | Kelly | B05B 11/3057 222/129 |
| 2014/0296124 | A1 | 10/2014 | Hulskotter et al. | |
| 2016/0067155 | A1 * | 3/2016 | Shimada | A61K 8/0212 424/44 |
| 2016/0068620 | A1 | 3/2016 | Tamareselvy et al. | |
| 2016/0075478 | A1 | 3/2016 | Godsey et al. | |
| 2016/0158776 | A1 * | 6/2016 | Sternberg | B65D 23/12 53/431 |
| 2016/0303043 | A1 * | 10/2016 | Khoury | A61K 47/26 |
| 2016/0355755 | A1 * | 12/2016 | Brooker | C11D 3/30 |
| 2017/0183609 | A1 | 6/2017 | Hulskotter et al. | |
| 2017/0226447 | A1 | 8/2017 | Keuleers et al. | |
| 2018/0037858 | A1 | 2/2018 | Keuleers et al. | |
| 2019/0093054 | A1 | 3/2019 | Patterson et al. | |
| 2019/0239506 | A1 | 8/2019 | Macinga et al. | |
| 2021/0128415 | A1 * | 5/2021 | Stern | A61Q 5/12 |
| 2021/0169750 | A1 | 6/2021 | Maka et al. | |
| 2021/0230519 | A1 * | 7/2021 | Watson | C11D 3/50 |
| 2021/0244632 | A1 | 8/2021 | Mehra et al. | |

OTHER PUBLICATIONS

International Search Report and Written Opinion dated Apr. 23, 2021 in PCT/US21/17629.

International Search Report and Written Opinion dated Jun. 8, 2021 in PCT/US21/17636.

* cited by examiner

WATER-SOLUBLE REFILL DOSE ARTICLE ENCLOSING A CONCENTRATED LIQUID CLEANSER COMPOSITION AND KITS HAVING SAME

The present application claims the benefit of U.S. Provisional Application 62/975,510 filed Feb. 12, 2020; which is hereby incorporated by reference in its entirety.

TECHNICAL FIELD

This application relates to a water-soluble refill dose article enclosing a concentrated cleanser composition, more particularly, to a water-soluble refill dose article dissolvable in water to form a liquid cleanser dispensable through a pump that forms foamed cleanser.

BACKGROUND

Many liquid cleansers, such as hand soaps, body wash, shampoos, etc., e.g., those in a filled hand soap dispenser or bottle, are intended for use with pumps that form a foam when activated. This is a preferred form for many consumers because of the experience of dispensing an expanded foam. These liquid cleansers, which are often sold in in bottles, pouches, or jugs with a large quantity of soap for refilling dispensers, have a large concentration of water, which contributes to the overall weight of a product. The weight of the product and size of the dispenser or container adds to the manufacturing, packaging costs, and shipping costs. Since clean water is readily available in most of the world and packaging can be re-used, it is wasteful to ship water in the liquid cleansers from one location to another and to use the original packages only once.

Liquid cleanser dispensers are useful in dispensing an appropriate amount of cleanser to a user for proper hygiene, including preventing the transmission of bacteria, viruses, etc. But refilling such dispensers can be difficult because of the heaviness of a bottle or jug of cleanser, which can make it difficult to hold and pour to fill the dispenser. It can also be messy, since dispensers typically have fairly small mouth openings.

It is a challenge to develop a concentrated cleanser, in a delivery vehicle that is convenient for consumers to use, that upon dilution with water, is easily soluble in water, achieves a viscosity acceptable for a dispenser that has an air pump to produce a foamed cleanser, and further still foams as expected by the user.

Such a concentrated form of a cleanser could be enclosed in water-soluble film that can be dissolved in water to form a suitable liquid cleanser to solve at least the above noted problems. The use of water-soluble film as a delivery vehicle introduces a multitude of additional challenges in formulating a shelf stable cleanser. For example, the concentrated cleanser must not prematurely dissolve the water-soluble film and must deliver a cleanser that has desirable viscosity and foamability.

SUMMARY

By encapsulating a cleanser as a concentrated, but diluteable formulation in a water soluble film or pouch, the above problems are overcome. In all aspects, water-soluble refill dose articles are disclosed that have a water-soluble film defining a first compartment enclosing a concentrated cleanser composition. The concentrated cleanser composition comprises an anionic surfactant, 0.1% by weight to 10% by weight water, and 20% or less by weight glycol. The anionic surfactant contributes to the % by weight water and the water-soluble refill dose article is added to water at a 1:1 to 1:20 ratio to form a cleanser volume and produces a liquid cleanser. The liquid cleanser is dispensable through a pump that forms foamed cleanser and has a viscosity within a range of 1 cps to 1000 cps. In all aspects, the concentrated cleanser concentration can be in the liquid phase. In all aspects, the anionic surfactant can be a foaming anionic surfactant present as 5% by wt to 33.3% by wt of the concentrated cleanser composition, and can be sodium laureth sulfate.

In one embodiment, the concentrated cleanser composition has a plurality of surfactants. The plurality of surfactants comprise sodium lauroyl sarcosinate, disodium cocoglucoside citrate, and polyglyceryl-2-caprate, which may be present in a ratio of 1:1:1 to 1.3:1:1.7.

In all aspects, the plurality of surfactants can include a nonionic surfactant. In one embodiment, the nonionic surfactant is polysorbate 20 and is present as less than 50% by weight of the concentrated liquid cleanser.

In all aspects, the concentrated cleanser composition comprises one or more additives selected from the group consisting of a coloring agent, a fragrance, an emollient, an emulsifier, and a preservative. In one or all embodiments, the preservative is phenoxyethanol.

In another aspect, cleanser dispensing kits are disclosed that have a dispenser that discharges a foamed cleanser upon activation by a user and a water-soluble refill dose article. The dispenser has a container defining a preselected cleanser volume and a pump removably and sealably engaging a mouth of the container. The pump foams a liquid cleanser upon activation of the pump, which may be hand-activated or sensor/automatically activated. The water soluble refill dose article has a water-soluble film defining a first compartment enclosing a concentrated cleanser composition. The concentrated cleanser composition comprises an anionic surfactant, 10% or less by weight water, and 20% or less by weight glycol. The anionic surfactant contributes to the % by weight water. The water-soluble refill dose article is added to water at a 1:1 to 1:20 ratio to form a cleanser volume and produces a liquid cleanser. The liquid cleanser is dispensable through a pump that forms foamed cleanser and has a viscosity within a range of 1 cps to 1000 cps. In all aspects, the concentrated cleanser concentration can be in the liquid phase. In all aspects, the anionic surfactant can be a foaming anionic surfactant is present as 5% by wt to 33.3% by wt of the concentrated cleanser composition, and can be sodium laureth sulfate.

The kit may have a water-soluble refill dose article disposed inside the dispenser and/or a plurality of the water-soluble refill dose articles packaged to accompany the dispenser. As such, the water-soluble refill dose article is sized and shaped to be smaller than the mouth of the container.

In one embodiment, the concentrated cleanser composition has a plurality of surfactants. The plurality of surfactants comprise sodium lauroyl sarcosinate, disodium cocoglucoside citrate, and polyglyceryl-2-caprate, which may be present in a ratio of 1:1:1 to 1.3:1:1.7.

In all aspects, the plurality of surfactants can include a nonionic surfactant. In one embodiment, the nonionic surfactant is polysorbate 20 and is present as less than 50% by weight of the concentrated liquid cleanser.

In all aspects, the concentrated cleanser composition comprises one or more additives selected from the group consisting of a coloring agent, a fragrance, an emollient, an emulsifier, and a preservative. In one or all embodiments, the preservative is phenoxyethanol.

DETAILED DESCRIPTION

Figure 1:
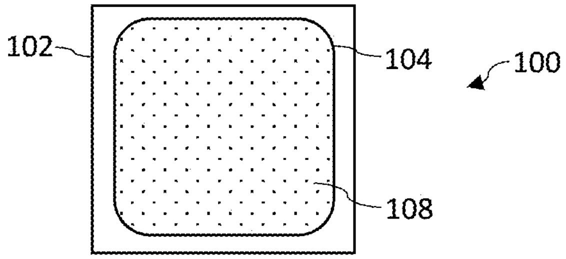
FIG. 1 is a top plan view of one embodiment of a water-soluble refill dose article that forms a liquid cleanser upon dilution in water that is dispensable through a pump that forms foamed cleanser.

The following detailed description will illustrate the general principles of the invention, examples of which are additionally illustrated in the accompanying drawings. In the drawings, like reference numbers indicate identical or functionally similar elements.

Except in the working examples, or where otherwise explicitly indicated, all numbers in this description indicating amounts, parts, percentages, ratios, and proportions of material, physical properties of material, and conditions of reaction are to be understood as modified by the word "about". "About" as used herein means that a value is preferably +/−5% or more preferably +/−2%.

As used herein "refill dose" means an amount of cleanser that is more than a single use volume. Typically, the refill dose defines a cleanser volume that includes a plurality of single use doses and may even form a refill cleanser volume that can fill multiple smaller sized dispensers.

All parts, percentages, ratios, and proportions of material referred to in this description are by weight unless otherwise indicated. It should also be noted that in specifying any range of concentration or amount, any particular upper concentration or amount can be associated with any particular lower concentration or amount.

FIG. 1 illustrates an embodiment of a water-soluble refill dose article 100 that forms a liquid cleanser upon dilution with water. The liquid cleanser may be a hand soap, body wash, shampoo, makeup remover, facial cleanser, dish soap, and the like. The water-soluble refill dose article 100 is made of a water-soluble film 102 defining a first compartment 104 enclosing a first composition 108. The first composition 108 comprises a first surfactant, has 10% or less by weight water, and 20% or less by weight glycol. The first surfactant can be a liquid or a solid, understanding that the solid will be dissolved or dispersed such that the composition can be in the liquid phase. Glycol as used herein means ethylene glycol, polyethylene glycol, derivatives thereof, and combinations thereof.

Figure 2:
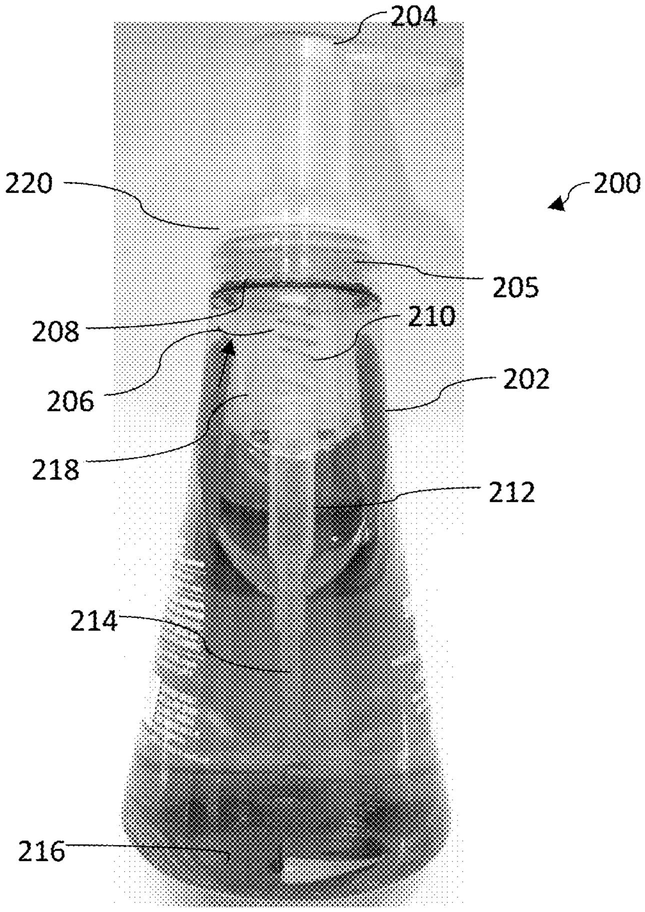
FIG. 2 is a photograph of one embodiment of a cleanser dispenser having a pump for forming foamed cleanser, which is partially filled with a liquid cleanser.

The water-soluble refill dose article 100 encloses a concentrated cleanser that when placed in a commercially available dispenser, for example, dispenser 200 of FIG. 2, and combined with water will create a liquid cleanser that after passing through the pump 204 is dispensed as a foamed cleanser. The water-soluble refill dose article is combined with water at a 1:1 to 1:20 ratio (refill dose article:water) to produce a cleanser volume that has a viscosity within a range of 1 cps to 1000 cps, more preferably 1 cps to 100 cps. The refill dose article:water is more preferably a 1:5 to 1:15 ratio, and even more preferably a 1:10 ratio. When diluted in water in a dispenser for a cleanser, such as a hand cleanser or body wash, the cleanser volume can be in a range of 50 ml to 18.9 L (5 gal), 100 ml to 7.6 L (2 gal), 100 mL to 1 L, 200 ml to 500 ml.

Methods for manufacturing a water-soluble refill dose article for forming a liquid cleanser are disclosed. A first vessel is provided that contains the first composition. Then, a first compartment is formed that is defined by a water-soluble film and encloses a first aliquot of the first composition. The first compartment when added to water at a 1:1 to 1:20 ratio produces a cleanser volume having a viscosity within a range disclosed above.

In another embodiment, methods for manufacturing a liquid cleanser on a commercial scale are disclosed. A first vessel is provided that contains the first composition. A second vessel is provided. A first aliquot of the first composition and water are introduced into the second vessel simultaneously or sequentially for dilution at a ratio of 1:1 to 1:20 to produce a liquid cleanser having a viscosity within a range disclosed above. The ratio with water is more preferably a 1:5 to 1:15 ratio, and even more preferably a 1:10 ratio. The manufacturing volume of the vessel may be any commercially reasonable size.

Referring again to FIG. 1, the water-soluble refill dose article comprises at least one water-soluble film shaped such that the refill dose article comprises at least one internal compartment surrounded by the water-soluble film. The first compartment holds on containment therein the first composition. The water-soluble film is sealed such that the first composition does not leak out of its compartment during storage. However, upon addition of the water-soluble refill dose article to water, the water-soluble film dissolves and releases the contents of the internal compartment into the water. A compartment should be understood as meaning a separate closed internal space defined by the water-soluble film, which encloses or encapsulates therein, in isolation, said composition.

The article may comprise two films. A first film may be shaped to comprise an open compartment into which the first composition is added. A second film is then laid over the first film in such an orientation as to close the opening of the compartment. The first and second films are then sealed together along a seal region. Suitable water-soluble films are described in more detail in U.S. Pat. Nos. 7,013,623 and 10,047,327, both of which are incorporated herein in their entirety.

The Concentrated Liquid Cleanser

The concentrated liquid cleanser composition has an anionic surfactant and optionally a plurality of surfactants, 0.1% by weight to 10% by weight water, and 20% or less by weight glycol. The anionic surfactant and optional at least two of the plurality of surfactants contribute to the % by weight water. The article is added to water or vice versa at a 1:1 to 1:20 ratio to define a cleanser volume and produce a liquid cleanser having a viscosity within a range of 1 cps to 1000 cps, more preferably 1 cps to 100 cps.

At least one of the plurality of surfactants or the anionic surfactant is a foaming surfactant. The foaming surfactant is present as 5% by wt to 33.3% by wt of the concentrated cleanser composition. A foaming surfactant is a surfactant that has as initial foam volume of greater than 10 cm per the Ross-Miles Foam Test (ASTM D1173-53). In one embodiment, the foaming anionic surfactant is sodium laureth sulfate.

The plurality of surfactants can include anionic, nonionic, and amphoteric surfactants. Many of the example surfactants below are foaming surfactants.

Examples of anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium lauroyl lactylate, sodium laureth sulfosuccinate, sodium lauroyl sulfosuccinate, sodium tridecyl benzene sulfonate, sodium dodecyl benzene sulfonate, sodium lauryl amphoacetate, sodium olefin sulfonate, sodium decyl sulfate, olivoil avenate, disodium coco-glucoside citrate, ammonium ether sulfate, laureth-5 carboxylic acid, potassium olivoyl hydrolyzed oat protein, and mixtures thereof. The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate. $C_8$-$C_{22}$ is a range for the length of the carbon chain, including any narrower ranges therein having a minimum and maximum selected from any of $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, and $C_{22}$.

Example nonionic surfactants include, but are not limited to, ethylene maleic anhydride (EMA), sorbitan stearate (e.g., SPAN® 60), sorbitan monooleate (e.g., SPAN® 80), polyethylene glycol sorbitan monooleate (TWEEN® 80), polysorbate (TWEEN® 20), polyvinyl alcohol, ethylene oxide/propylene oxide block copolymers (e.g., PLURONIC® P105), polyoxyethylene (5) nonylphenylether, branched (IGEPAL® CO-520), alcohol ethoxylate, linear alcohol (C9-11) ethoxylate, decyl alcohol ethoxylate, sodium cocoyl glutamate, polyglyceryl-2-caprate, polyglyceryl-3 lactate/laurate, or a mixture thereof. Additionally, polyethylene glycol (PEG), glyceryl, or glycol ethers of fatty alcohols can be used.

Amphoteric surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amphoteric surfactants are coco dimethyl carboxymethyl betaine, cocoamidopropyl betaine, cocobetaine, cocamidopropyl hydroxysultaine, oleyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

In one embodiment, the surfactants combined with the foaming anionic surfactant include one or more additional anionic surfactant. The one or more anionic surfactants can be selected from sodium lauroyl sarconsinate, disodium coco-glucoside citrate, and olivoil avenate. In another embodiment, the mixture of surfactants comprises sodium lauroyl sarcosinate, disodium coco-glucoside citrate, and polyglyceryl-2-caprate, which can be present in a ratio of 1:1:1 to 1.3:1:1.7.

In another embodiment, the mixture of surfactants combined with the foaming anionic surfactant includes a nonionic surfactant such as polysorbate 20. The polysorbate is present as less than 50% by weight of the concentrated liquid cleanser, for example, in a range of 0.1% by weight to 50% by weight, preferably 1% by weight to 20% by weight, and more preferably 5% by weight to 15% by weight.

Each surfactant may be present as a liquid or a solid, understanding that any solids will ultimately be dissolved in water. In one embodiment, a solid surfactant is dissolved or dispersed in another component of the concentrated cleanser composition, such that the concentrated cleaner composition is in the liquid phase. Some examples of solid surfactants include, but are not limited to PEG-7 glyceryl cocoate, sodium lauroyl sarcosinate, and sodium $C_{14}$-$C_{16}$ alpha olefin sulfonate.

Preservative

The first composition comprises a preservative in a total effective amount for the preselected cleanser volume. The "total effective amount" is the total amount of preservative in the one or more compartments that upon dilution with water to the preselected cleanser volume is present in a preservative effective amount to give the preselected cleanser volume a shelf-life suitable to industry standards. The total effective amount of the preservative is in a range of 1% by weight to 25% by weight and the amount of preservative in the preselected cleanser volume is in a range of 0.1% by weight to 2% by weight.

The preservatives protect the resulting liquid cleanser against the growth of potentially harmful microorganisms. Suitable preservatives include, but are not limited to, alkyl esters of para-hydroxybenzoic acid, hydantoin derivatives, propionate salts, and a variety of quaternary ammonium compounds. Among the preservatives of particular interest are phenoxyethanol, methyl paraben, propyl paraben, imidazolidinyl urea, sodium dehydroacetate and benzyl alcohol.

Additives

The first composition can comprise one or more additives. The additives may be selected from the group consisting of coloring agents, fragrances, skin and/or hair benefit agents, UV absorbers, and emulsifiers.

The term skin and/or hair benefit agent, collectively "benefit agents," is typically a substance which softens or improves the elasticity, appearance, and youthfulness of the skin (stratum corneum) by either increasing its water content, adding, or replacing lipids and other skin nutrients, or both, and keeps it soft by retarding the decrease of its water content. For hair, the benefit agent is typically a substance that conditions, strengthens, repairs, smooths, reduces static, imparts style-retention properties, color, or provides another benefit to the hair. Included among the suitable skin benefit agents are emollients, including, for example, hydrophobic emollients, hydrophilic emollients, or blends thereof.

Useful benefit agents include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, and mink oils; cacao fat; beef tallow and lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) hydrophobic and hydrophilic plant extracts; (e) hydrocarbons such as liquid paraffin, petrolatum, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol monolaurate, glycerol distearate, glycerol tristearate, alkyl lactate, alkyl citrate and alkyl tartrate; (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, shea oil, menthol, cineole, eugenol, citral, citronelle, borneol, linalool, geraniol, evening primrose, camphor, thymol, spirantol, penene, limonene and terpenoid oils; (j) polyhydric alcohols, for example, glycerine, sorbitol, propylene glycol, and the like; and polyols such as the polyethylene glycols, examples of which are: Polyox WSR-205 PEG 14M, Polyox WSR-N-60K PEG 45M, or Polyox WSR-N-750, and PEG 7M; (k) lipids such as cholesterol, ceramides, sucrose esters and pseudo-ceramides as described in European Patent Specification No. 556,957; (1) vitamins, minerals, and skin nutrients such as milk, vitamins A, E, and K; vitamin alkyl esters, including vitamin C alkyl esters; magnesium, calcium, copper, zinc and other metallic components; (m) sunscreens such as octyl methoxyl cinnamate (Parsol MCX) and butyl methoxy benzoylmethane (Parsol 1789); (n) phospholipids; (o) anti-aging compounds such as alpha-hydroxy acids and beta-hydroxy acids; and (p) quaternary ammonium compounds such as cetyl trimethyl ammonium bromide, myristyl trimethyl ammonium bromide, stearyl dimethyl benzyl ammonium chloride, lauryl/myristryl trimethyl ammonium methosulfate, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, cocoyl hydroxyethylimidazolinium.

Example hair benefit agents are found in US 2003/0161796, and example skin and hair benefit agents are found in U.S. Pat. No. 8,105,994. The examples from both patent references are incorporated herein by reference.

Benefit agents commonly account for up to 30% weight of the preselected cleanser volume, with levels of from 0% to 25% weight, more particularly from 0% to 20% weight, being typical of the levels at which those skin benefit agents generally known as "emollients" are employed in many of the subject formulations. Preferred skin benefit agents include fatty acids, hydrocarbons, polyhydric alcohols, polyols and mixtures thereof, with emollients that include at least one $C_{12}$ to $C_{18}$ fatty acid, petrolatum, glycerol, sorbitol and/or propylene glycol.

Additional optional ingredients which may be present in the cleansing formulations are, for example: sequestering and chelating agents such as tetrasodium ethylenediaminetetraacetate (EDTA), ethane hydroxyl diphosphonate (EHDP), and etidronic acid, aka 1-hydroxyethylidene diphosphonic acid (HEDP); opacifiers and pearlizers such as zinc stearate, magnesium stearate, $TiO_2$, ethylene glycol monostearate (EGMS), ethylene glycol distearate (EGDS) or Lytron 621 (Styrene/Acrylate copolymer) and the like; pH adjusters; antioxidants, for example, butylated hydroxytoluene (BHT) and the like; stabilizers such as benzotriazolyl dodecyl p-cresol (a broadband UV absorber for stabilization of transparent packaged products); and other ingredients such as are conventionally used in liquid cleanser formulations. The total amount of such additional optional ingredients is typically from 0% to 10% by weight, more particularly from 0.1% to 5% by weight, based on the total weight of the cleanser volume.

If desired, an additional compartment or a subchamber formed of water-soluble film can be included to enclose any desirable single or multi-component formulation to provide a preselected attribute to the concentrated cleanser once diluted with water.

Kit

The water-soluble refill dose articles 100 comprise a concentrated cleanser formulation that when placed in a vessel, such as dispenser 200 of FIG. 2, and combined with water will create a liquid cleanser that is dispensable through a pump that forms foamed cleanser to dispense a foamed amount of the cleanser.

Liquid cleanser-dispenser kits include a dispenser that discharges a foamed cleanser upon activation by a user and a water-soluble refill dose article as described above. Referring to FIG. 2, a dispenser 200 has a container 202 defining a preselected volume, as noted by the fill line 206, and a pump 204 that is removably and sealably engaging a mouth 208 of the container, for example, by a threaded neck 205 seen through the clear plastic threaded collar 220 of the pump 204. The pump 204 includes a spring 210 seated inside a larger diameter tube 212, which are both positioned inside an air pump chamber 218 that is in fluid communication with the pump 204. A smaller diameter tube 214 is inserted in the larger diameter tube and extends to or toward an interior bottom 216 of the container 202. Example dispensers that generate a foamed cleanser by mixing a liquid cleanser with air upon activation of a pump are disclosed in U.S. Pat. Nos. 6,840,408 and 6,923,346, which are both incorporated herein by reference in their entirety.

The water-soluble refill dose article 100 is dissolvable in water to form a liquid cleanser having a preselected volume and having a viscosity within a range of 1 cps to 1000 cps, more preferably 1 cps to 100 cps. And, after water is added to the container 202 to the fill line 206, the water-soluble refill dose article dissolves to form a liquid cleanser within the dispenser 200. Gentle swishing by the user will aid in the mixing and dissolving of the water-soluble refill dose article.

The pump 204 of the dispenser is a hand-actuatable pump, but may include a sensor for automatic dispensing of the cleanser. The fill line 206 identifies a preselected volume for the container 202, for example, any of the volumes discussed above. However, the size and shape of the dispenser can be selected to fit the user's needs.

The kit may have one water-soluble refill dose article disposed inside the container of the dispenser, without water present, at the point of sale. The kit may include one or more additional water-soluble refill dose articles accompanying the dispenser. Alternately, the kit may include an empty dispenser and a packet containing a plurality of water-soluble refill dose articles.

The water-soluble refill dose article is sized and shaped to be smaller than the mouth 208 of the container 202. In an embodiment for a free-standing, bathroom countertop dispenser, the water-soluble refill dose article is generally cylindrically shaped and has a diameter less than 5 cm, more preferably less than 3 cm.

Working Examples

The Formulation in Table 1 is for a 1:10 volume dilution to form a liquid cleanser that is suitable for dispensing through a foam pump of a dispenser that forms a foamed cleanser.

TABLE 1

| First Composition for First Compartment | Minimum | Example 1 (% wt/wt) | Maximum |
|---|---|---|---|
| Surfactant Blend | (20%) | (60%) | (80%) |
| 'propylene glycol | 5% | 15% | 20% |
| 'disodium coco-glucoside citrate | 5% | 15% | 20% |
| 'sodium lauroyl sarcosinate | 4% | 12% | 16% |
| 'polyglyceryl-2-Caprate | 5% | 15% | 20% |
| 'water (A) | 1% | 3% | 4% |
| sodium laureth sulfate (70%) | 5% | 7% | 33.3% |
| 'water (B) | 1.5% | 3% | 10% |
| Olivoil Avenate Surfactant (25-35%) | 0% | 0.7% | 3.5% |
| 'water (C) | 0% | 1.3% | 6.5% |
| Shebu Oil | 0% | 0.3% | 10% |
| Phenoxyethanol | 0.1 | 11% | 20% |
| polysorbate 20 | 0% | 10.7% | 48.5% |
| 'water (D) | 0% | 0.3% | 1.5% |
| Fragrance | 0% | 5.7% | 30% |
| | | 100.0% | |

In the composition of Table 1, the percent by weight of water is 10% or less, i.e., the sum of the weight percent of water (A), water (B), water (C), and water (D) equals at most 10% wt/wt. A minimum value of 0% is used to demonstrate that the particular substance is optional. However, when such optional substances are present, the minimum may be 0.1% by weight or 1% by weight, or 2% by weight, or 3% by weight, or 4% by weight, or 5% by weight.

For Example 1 above, at room temperature (typically about 25° C.), in a main vessel the phenoxyethanol and Shebu oil were mixed until uniform. Next, the surfactant blend was added with mixing. Then, the other surfactants, i.e., the sodium laureth sulfate and the olivoil avenate surfactant, were added to the main vessel with mixing. In a separate vessel any fragrance(s) were mixed with the polysorbate 20. Then, the polysorbate 20 mixture was added to the main vessel with mixing. Lastly, any colorants were added with mixing until a uniform solution was formed.

By encapsulating the liquid cleanser as a concentrated, but diluteable formulation in a water-soluble film or pouches, the packaging weight of the product and its size is reduced for reduced shipping and packaging costs. The product can be shipped to any location, placed into a dispenser container, and, upon filling the same with water, dissolved in water to form a liquid cleanser dispensable through a foaming pump.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Having described the invention in detail and by reference to preferred embodiments thereof, it will be apparent that modifications and variations are possible without departing from the scope of the invention which is defined in the appended claims.

What is claimed is:

1. A water-soluble refill dose article comprising:

a water-soluble film defining a first compartment, which is a separate closed internal space, in which a concentrated liquid cleanser composition is encapsulated in isolation;

wherein adding the article to water at a 1:1 up to a 1:20 ratio by volume dilution defines a cleanser volume and produces a liquid cleanser dispensable through a pump that forms foamed cleanser and having a viscosity within a range of 1 cps to 1000 cps;

wherein the concentrated liquid cleanser composition comprises:

5% by weight to 33.3% by weight of an anionic surfactant selected from the group consisting of a sulfate, a sulfonate, a sulfosuccinate, a taurate, an isethionate, an amphoacetate, and combinations thereof;

20% by weight to 80% by weight of a surfactant blend consisting of:

sodium lauroyl sarcosinate, disodium coco-glucoside citrate, polyglyceryl-2-caprate, and propylene glycol;

optionally polysorbate 20 and/or olivoil avenate;

a preservative in an effective amount for the cleanser volume; and 0.1% by weight to 10% by weight water;

wherein the propylene glycol is present as 5% by weight to 20% by weight of the concentrated liquid cleanser composition; and wherein the anionic surfactant and/or surfactant blend contribute to the % by weight water.

2. The article of claim 1, wherein the anionic surfactant is sodium laureth sulfate.

3. The article of claim 1, wherein the sodium lauroyl sarcosinate, disodium coco-glucoside citrate and polyglyceryl-2-caprate are present in a weight ratio of 1:1:1 to 1.3:1:1.7.

4. The article of claim 1, wherein the olivoil avenate is present in the concentrated liquid cleanser composition.

5. The article of claim 1, wherein the polysorbate 20 is present in the concentrated liquid cleanser composition.

6. The article of claim 5, wherein the polysorbate is present as less than 50% by weight of the concentrated liquid cleanser composition.

7. The article of claim 1, the concentrated liquid cleanser composition further comprises one or more additives selected from the group consisting of a coloring agent, a fragrance, an emollient, and an emulsifier.

8. A cleanser dispensing kit comprising:

a dispenser that discharges a foamed cleanser upon activation by a user, the dispenser comprising:

a container defining a preselected cleanser volume and a pump removably and sealably engaging a mouth of the container, wherein the pump foams a liquid cleanser; and a water-soluble refill dose article comprising:

a water-soluble film defining a first compartment, which is a separate closed internal space, in which a concentrated liquid cleanser composition is encapsulated in isolation;

wherein, upon addition of the article and water to the preselected cleanser volume within the container, a liquid cleanser having a viscosity within a range of 1 cps to 1000 cps is formed that is dispensable through the pump as a foamed cleanser;

the concentrated liquid cleanser composition comprises:

5% by weight to 33.3% by weight of an anionic surfactant selected from the group consisting of a sulfate, a sulfonate, a sulfosuccinate, a taurate, an isethionate, an amphoacetate, and combinations thereof;

20% by weight to 80% by weight of a surfactant blend consisting of:

sodium lauroyl sarcosinate, disodium coco-glucoside citrate, polyglyceryl-2-caprate, and propylene glycol;

optionally polysorbate 20 and/or olivoil avenate;

a preservative in an effective amount for the cleanser volume; and 0.1% by weight to 10% by weight water;

wherein the propylene glycol is present as 5% by weight to 20% by weight of the concentrated liquid cleanser composition; and wherein the anionic surfactant and/or surfactant blend contribute to the % by weight water; and wherein the water-soluble refill dose article has an article to water ratio in a range of 1 article to 20 water by volume dilution to produce the preselected cleanser.

9. The kit of claim 8, wherein the water-soluble refill dose article is disposed inside the dispenser.

10. The kit of claim 8, wherein the water-soluble refill dose article is sized and shaped to be smaller than the mouth of the container.

11. The kit of claim 8, comprising a plurality of the water-soluble refill dose articles.

12. The kit of claim 8, wherein the pump is a hand-actuatable pump.

13. The kit of claim 8, wherein the anionic surfactant is sodium laureth sulfate.

14. The kit of claim 8, wherein the sodium lauroyl sarcosinate, disodium coco-glucoside citrate and polyglyceryl-2-caprate are present in a weight ratio of 1:1:1 to 1.3:1:1.7.

15. The kit of claim 8, wherein the olivoil avenate is present in the concentrated liquid cleanser composition.

16. The kit of claim 8, wherein the polysorbate 20 is present in the concentrated liquid cleanser composition.

17. The kit of claim 16, wherein the polysorbate is present as less than 50% by weight of the concentrated liquid cleanser composition.

18. The kit of claim 8, the concentrated liquid cleanser composition further comprises one or more additives selected from the group consisting of a coloring agent, a fragrance, an emollient, and an emulsifier.

* * * * *